United States Patent
Matsumoto et al.

(10) Patent No.: US 10,073,076 B2
(45) Date of Patent: *Sep. 11, 2018

(54) PHOTOSTIMULATION DEVICE AND PHOTOSTIMULATION METHOD

(71) Applicant: HAMAMATSU PHOTONICS K.K., Hamamatsu-shi, Shizuoka (JP)

(72) Inventors: Naoya Matsumoto, Hamamatsu (JP); Koyo Watanabe, Hamamatsu (JP); Hirotoshi Terada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/312,054

(22) PCT Filed: May 20, 2015

(86) PCT No.: PCT/JP2015/064481
§ 371 (c)(1),
(2) Date: Nov. 17, 2016

(87) PCT Pub. No.: WO2015/178420
PCT Pub. Date: Nov. 26, 2015

(65) Prior Publication Data
US 2017/0082597 A1 Mar. 23, 2017

(30) Foreign Application Priority Data
May 21, 2014 (JP) .................................. 2014-105422

(51) Int. Cl.
G01B 21/00 (2006.01)
G01N 33/483 (2006.01)
(Continued)

(52) U.S. Cl.
CPC ......... *G01N 33/4833* (2013.01); *G01B 11/24* (2013.01); *G01N 21/41* (2013.01);
(Continued)

(58) Field of Classification Search
CPC ........ G01B 11/24; G01N 21/00; G01N 21/45; G01N 21/41
See application file for complete search history.

(56) References Cited

U.S. PATENT DOCUMENTS

2009/0125242 A1* 5/2009 Choi ..................... G01N 21/45
702/19
2017/0089837 A1* 3/2017 Matsumoto ........ G01N 21/6458

FOREIGN PATENT DOCUMENTS

CN 100388043 5/2008
CN 102829718 12/2012
(Continued)

OTHER PUBLICATIONS

M. Booth et. al., "Adaptive Optics for Biomedical Microscopy", OPN Optics & Photonics News, vol. 23, Issue 1, Jan. 1, 2012, p. 22-p. 29.
(Continued)

*Primary Examiner* — Jonathan Hansen
(74) *Attorney, Agent, or Firm* — Drinker Biddle & Reath LLP

(57) ABSTRACT

A photostimulation apparatus includes an objective lens arranged to face a biological object, a light source configured to output light to be radiated toward the biological object via the objective lens, a shape acquisition unit configured to acquire information about a shape with a refractive index difference in the biological object, a hologram generation unit configured to generate aberration correction hologram data for correcting aberrations due to the shape with the refractive index difference on the basis of the
(Continued)

information acquired by the shape acquisition unit, and a spatial light modulator on which a hologram based on the aberration correction hologram data is presented and which modulates the light output from the light source.

8 Claims, 16 Drawing Sheets

(51) Int. Cl.
    *G01B 11/24*     (2006.01)
    *G02B 21/00*     (2006.01)
    *G01N 21/41*     (2006.01)
    *G02B 5/32*     (2006.01)
    *G02B 27/00*     (2006.01)
    *G03H 1/00*     (2006.01)
    *G03H 1/08*     (2006.01)
    *G03H 1/22*     (2006.01)
    *G01N 21/64*     (2006.01)
    *G01N 21/63*     (2006.01)

(52) U.S. Cl.
    CPC ........... *G01N 21/6458* (2013.01); *G02B 5/32* (2013.01); *G02B 21/00* (2013.01); *G02B 27/0068* (2013.01); *G03H 1/0005* (2013.01); *G03H 1/08* (2013.01); *G03H 1/2294* (2013.01); *G01N 21/636* (2013.01); *G01N 21/6486* (2013.01); *G01N 2021/6471* (2013.01); *G01N 2201/0675* (2013.01)

(56) References Cited

FOREIGN PATENT DOCUMENTS

| | | |
|---|---|---|
| JP | 2010-058128 A | 3/2010 |
| JP | 2011-180290 A | 9/2011 |
| JP | 2011-239884 A | 12/2011 |
| JP | 2012-533069 A | 12/2012 |
| JP | 2015-060202 A | 3/2015 |
| WO | WO-2011/006106 A1 | 1/2011 |
| WO | WO-2013/061961 A1 | 5/2013 |
| WO | WO-2014/041660 A1 | 3/2014 |

OTHER PUBLICATIONS

E. Boyden et al, "Millisecond-timescale, genetically targeted optical control of neural activity", Nature Neuroscience, vol. 8, No. 9, 2005, p. 1263-p. 1268.
Y. Tamada et al., "Development of Adaptive Optics Microscopy for Fine Live Imaging", Genes & Genetic Systems, vol. 88(2013, No. 6, May 1, 2014, p. 387.
U.S. Office Action dated Jul. 28, 2017 that issued in U.S. Appl. No. 15/311,912 including Double Patenting Rejections on pp. 2-3.
International Preliminary Report on Patentability dated Dec. 1, 2016 for PCT/JP2015/064481.
JP Office Action dated Jun. 12, 2018 that issued in counterpart application JP Patent Application No. P2014-105422, along with its English-language translation attached.

* cited by examiner (a)

(b)

(a)

(b)

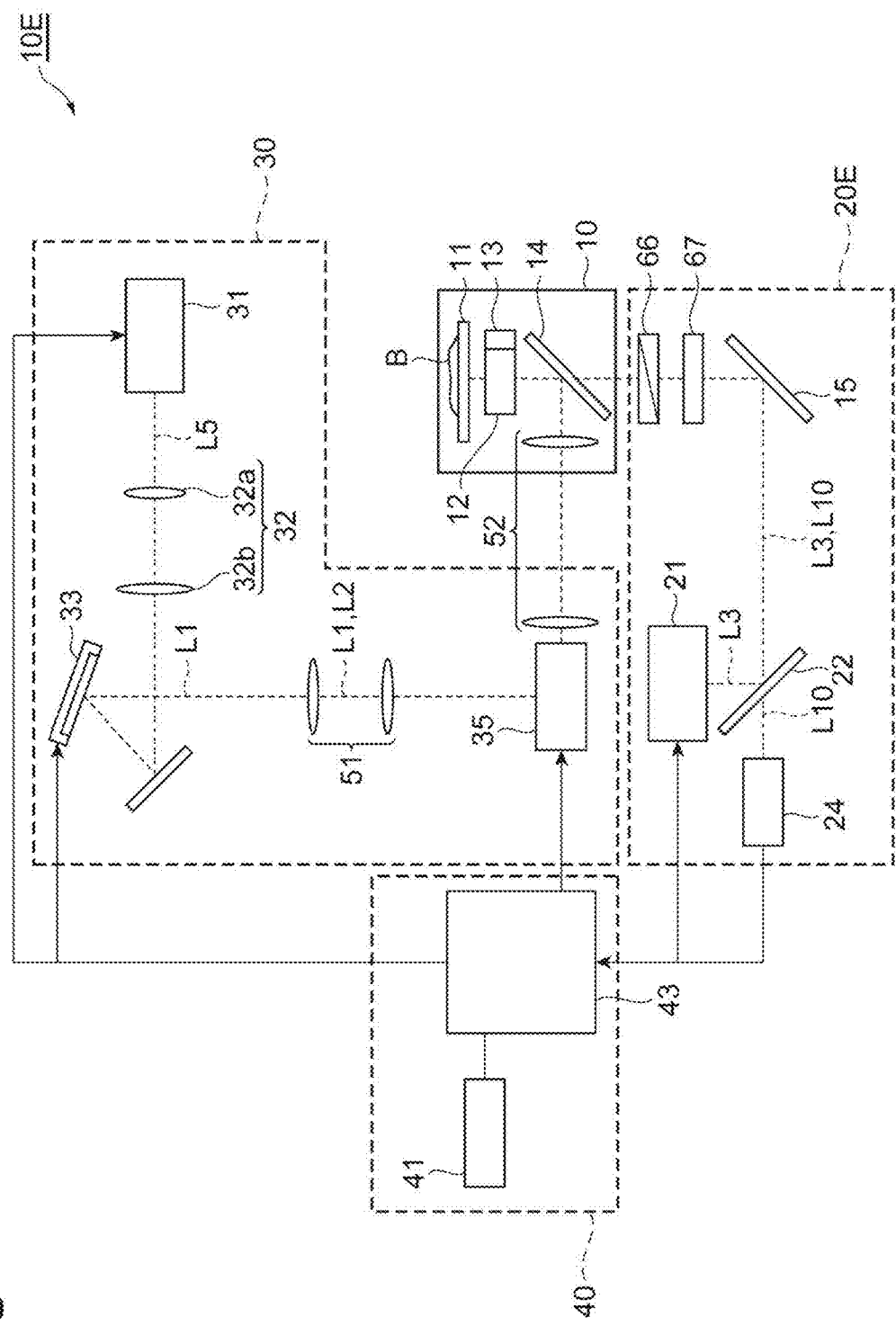

PHOTOSTIMULATION DEVICE AND PHOTOSTIMULATION METHOD

TECHNICAL FIELD

One aspect of the present invention relates to a photostimulation apparatus and a photostimulation method.

BACKGROUND ART

Non-Patent Literature 1 discloses technology for controlling opening and closing of a channel of sodium ions and chloride ions of neural cells by applying photostimulation of a specific wavelength to mammalian neural cells in which channelrhodopsin-2 (ChR2) and halorhodopsin (NpHR), which are photosensitive ion channel proteins from green algae, appear.

CITATION LIST

Non-Patent Literature

[Non-Patent Literature 1] E. S. Boyden et al., "Millisecond-timescale, genetically targeted optical control of neural activity", Nature Neuroscience, 1263-8, (2005)

SUMMARY OF INVENTION

Technical Problem

Recently, optogenetics for inspecting a function of an internal organ such as a neural circuit or the like, acquiring a function, or causing a loss by performing photostimulation on biological objects such as mammals, other animals, and plants has been studied. It is necessary to control photostimulation in optogenetics with millisecond-order time precision at a desired position within a living body.

However, in many cases, a surface of a biological object is not flat. Accordingly, aberrations occur due to a surface shape of the biological object. The biological object is constituted of blood vessels, tissues, etc. Thus, materials such as red blood cells and lipids having different refractive indices are present in the biological object. Accordingly, aberrations occur inside the biological object. As described above, the aberrations occur due to a shape with a refractive index difference in the biological object. If irradiation light is affected by the aberrations, a condensed light intensity of the irradiation light is weakened at a desired irradiation position within the biological object or a condensed light range spreads. Thus, there is a problem in that it is difficult to perform photostimulation limited to a desired irradiation position.

One aspect of the present invention has been made in view of the such problems, and an object thereof is to provide a photostimulation apparatus and a photostimulation method capable of suppressing a decrease in condensing intensity of irradiation light inside a biological object and spreading of a condensing shape.

Solution to Problem

To solve the above-described problem, a photostimulation apparatus according to an aspect of the present invention is a apparatus for stimulating a biological object by irradiating with light, the apparatus including: an objective lens arranged to face the biological object; a light source for outputting light with which the biological object is irradiated via the objective lens; a shape acquisition unit for acquiring information on a shape of the biological object with a refractive index difference; a hologram generation unit for generating aberration correction hologram data for correcting an aberration due to the shape with the refractive index difference on the basis of the information acquired by the shape acquisition unit; and a spatial light modulator to which a hologram based on the aberration correction hologram data is presented and for modulating the light output from the light source.

A photostimulation method according to an aspect of the present invention is a method for stimulating a biological object by irradiating with light, the method including: a step of acquiring information on a shape of the biological object facing an objective lens with a refractive index difference (shape acquisition step); a step of generating aberration correction hologram data for correcting aberrations due to the shape with the refractive index difference on the basis of the information acquired in the shape acquisition step (hologram generation step); and a step of presenting a hologram to a spatial light modulator based on the aberration correction hologram data, modulating light output from a light source by the spatial light modulator, and irradiating the biological object with the light after modulation (optical irradiation step).

In the photostimulation apparatus and the photostimulation method described above, the information about the shape (e.g., a surface shape or a structure directly under a surface) with the refractive index difference in the biological object is obtained. On the basis of the information, the aberration correction hologram data for correcting aberrations is generated. Irradiation light is modulated by a hologram based on the data. Thereby, it is possible to suppress a decrease in condensing intensity of irradiation light inside a biological object and spreading of a condensing shape because the shape with the refractive index difference in the biological object is preferably corrected.

In the photostimulation apparatus and the photostimulation method described above, the shape with the refractive index difference may include the surface shape of the biological object. According to the photostimulation apparatus and the photostimulation method described above, for example, in this case, it is possible to suppress a decrease in condensing intensity of irradiation light inside a biological object and spreading of a condensing shape.

In the photostimulation apparatus and the photostimulation method described above, the shape with the refractive index difference may include the structure directly under the surface of the biological object. According to the photostimulation apparatus and the photostimulation method described above, for example, in this case, it is possible to preferably suppress a decrease in condensing intensity of irradiation light inside a biological object and spreading of a condensing shape.

In the above-described photostimulation apparatus, the hologram generation unit performs a wavefront calculation using geometrical optics, wave optics, or electromagnetic field analysis on the basis of the information to generate the aberration correction hologram data. Likewise in the above-described photostimulation method, in the hologram generation step, the aberration correction hologram data may be generated by performing a wavefront calculation using geometrical optics, wave optics, or electromagnetic field analysis.

Advantageous Effects of Invention

According to the photostimulation apparatus and the photostimulation method according to the aspects of the present invention, it is possible to suppress a decrease in condensing intensity of irradiation light inside a biological object and spreading of a condensing shape.

BRIEF DESCRIPTION OF DRAWINGS

FIG. 16 is a diagram illustrating a configuration of a photostimulation apparatus according to a sixth modification example.

DESCRIPTION OF EMBODIMENTS

Figure 1:
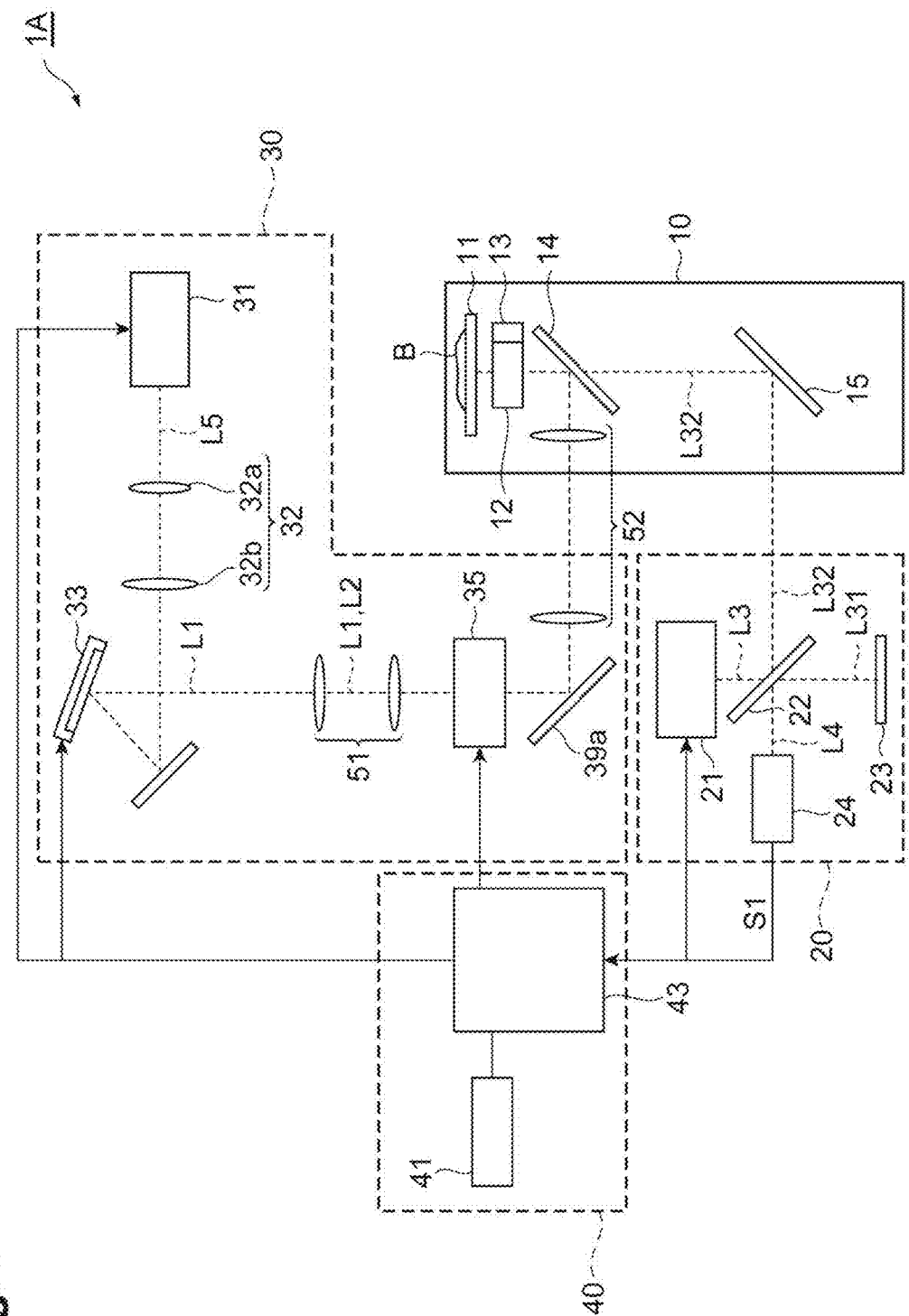
FIG. 1 is a diagram illustrating a configuration of a photostimulation apparatus according to a first embodiment.

Hereinafter, embodiments of a photostimulation apparatus and an photostimulation method according to an aspect of the present invention will be described with reference to the accompanying drawings. In the description of the drawings, the same elements are denoted with the same reference numerals, and repeated description will be omitted.

First Embodiment

FIG. 1 is a diagram illustrating a configuration of a photostimulation apparatus 1A according to an embodiment of one aspect of the present invention. The photostimulation apparatus 1A is an apparatus for acquiring an image of a biological object B by irradiating with light. The photostimulation apparatus 1A includes an optical irradiation unit 10, a shape measurement unit 20, an irradiation light generation unit 30, and a control unit 40, as illustrated in FIG. 1.

The optical irradiation unit 10 irradiates the biological object B with light from a shape measurement unit 20 and an irradiation light generation unit 30, which will be described below, and outputs light from the biological object B to the shape measurement unit 20. The optical irradiation unit 10 includes a biological object table 11, an objective lens 12, an objective lens moving mechanism 13, a beam splitter 14, and a reflective mirror 15.

The biological object table 11 is a plate-like member for supporting the biological object B (or a vessel that accommodates the biological object B). The biological object table 11 is formed of, for example, a material that transmits the irradiation light L1, such as glass or plastic. The biological object table 11 is, for example, a glass slide, a bottomed dish, or a microplate. In this embodiment, the irradiation light L1 is radiated to a back surface of the biological object table 11, transmitted through the biological object table 11, and radiated to the biological object B.

The objective lens 12 is disposed to face the biological object B, and condenses the irradiation light L1 on the inside of the biological object B. If the light from the biological object B (e.g., fluorescent light, generated harmonic waves, reflected light, transmitted light, or the like, hereinafter referred to as light to be detected) is observed in the irradiation light generation unit 30, an objective lens for the irradiation light L1 and an objective lens for the light to be detected may be individually provided. For example, an objective lens having a high numerical aperture (NA) may be used for the irradiation light L1 and locally focused by aberration correction. Further, an objective lens having a large pupil may be used for the light to be detected to extract a larger amount of light. The objective lens for the irradiation light L1 and the objective lens for the light to be detected may be arranged so that the biological object B is interposed therebetween and transmitted light in the biological object B of the irradiation light L1 may be acquired as the light to be detected.

The objective lens moving mechanism 13 is a mechanism for moving the objective lens 12 in the optical axis direction of the irradiation light L1. The objective lens moving mechanism 13 includes a stepping motor, a piezo-actuator, or the like.

The beam splitter 14 divides and combines an optical path between the optical irradiation unit 10 and the irradiation light generation unit 30 and an optical path between the optical irradiation unit 10 and the shape measurement unit 20. Specifically, the beam splitter 14 reflects the irradiation light L1 reaching the optical irradiation unit 10 from the irradiation light generation unit 30, toward the objective lens 12. The beam splitter 14 transmits light L32 from the shape measurement unit 20 and reflected light of the light L32 in the biological object B. The beam splitter 14 may include, for example, a half mirror or a dichroic mirror. The reflective mirror 15 is provided to change an optical axis direction of the light L32, as necessary.

The shape measurement unit 20 is a shape acquisition unit in this embodiment. The shape measurement unit 20 includes a detector 24, and is optically coupled to the objective lens 12. The shape measurement unit 20 acquires information on a shape with a refractive index distribution of the biological object B, that is, information on a surface shape of the biological object B (a shape according to a refractive index difference due to the biological object B and the surrounding (air)). The shape measurement unit 20 may be, for example, an interference light measurement unit that measures the surface shape of the biological object B using a Michelson interferometer. In this case, the shape measurement unit 20 includes a coherent light source 21, a beam splitter 22, a reference light mirror 23, and a detector 24, as illustrated in FIG. 1.

The coherent light source 21 generates coherent light L3 with which the biological object B is irradiated. The coherent light source 21 preferably includes, for example, a semiconductor laser element.

The beam splitter 22 causes the coherent light L3 from the coherent light source 21 to separate into reference light L31 and light L32 directed to the optical irradiation unit 10. Further, the beam splitter 22 reflects the reference light L31 reflected by the reference light mirror 23 and transmits reflected light from the surface of the biological object B of the light L32. Accordingly, the beam splitter 22 combines the lights to generate interference light L4. The interference light L4 is input to the detector 24. The reference light mirror 23 may be configured to be movable with respect to the optical axis direction of the reference light L31 or may be fixed.

The detector 24 detects the interference light L4 combined by the beam splitter 22 and outputs a detection signal S1. The detector 24 includes a two-dimensional photodetector such as a CCD image sensor or a CMOS image sensor.

The shape measurement unit is not limited to the configuration of this embodiment. For example, the shape measurement unit may use an interference measurement scheme such as a Mirau type or a Linnik type. Alternatively, the shape measurement unit may include a confocal reflectance microscope or may include a common path interferometer. According to such a microscope, it is possible to preferably measure the surface shape of the biological object B using focusing information. Further, the shape measurement unit may use evanescent light. Accordingly, shape recognition such as recognition as to whether or not the biological object B is grounded on the biological object table 11 is facilitated.

The irradiation light generation unit 30 generates the irradiation light L1 to be radiated toward the biological object B. The irradiation light generation unit 30 of this embodiment includes a laser light source 31, a beam expander 32, a spatial light modulator (SLM) 33, and an optical scanner 35.

The laser light source 31 is a light irradiation unit in this embodiment, and irradiates the biological object B with light L5 via the objective lens 12. The laser light source 31 is a light source that outputs the light L5 with which the biological object B is irradiated via the objective lens 12. The laser light source 31 is optically coupled to the objective lens 12. The light L5 is, for example, laser light including light with a wavelength to be radiated to the biological object B. The laser light source 31 includes, for example, a semiconductor laser element. The beam expander 32 includes, for example, a plurality of lenses 32a and 32b arranged side by side on an optical axis of the light L5, and adjusts a size of a cross-section perpendicular to the optical axis of the light L5.

A spatial light modulator 33 is optically coupled to the laser light source 31. The spatial light modulator 33 presents a hologram including an aberration correction hologram for correcting an aberration caused by the surface shape of the biological object B. The spatial light modulator 33 modulates the light L5 from the laser light source 31 to generate the irradiation light L1 with which the biological object B is irradiated. The surface shape of the biological object B is measured by the shape measurement unit 20 described above. The spatial light modulator 33 may be of a phase modulation type or of an amplitude (intensity) modulation type. Further, the spatial light modulator 33 may be either of a reflection type or of a transmission type. The aberration correction hologram will be described in detail below.

The optical scanner 35 scans an irradiation position of the irradiation light L1 in the biological object B by moving an optical axis of the irradiation light L1 within a plane perpendicular to the optical axis of the irradiation light L1. The optical scanner 35 includes, for example, a galvanometer mirror, a resonant mirror, a MEMS mirror, or a polygon mirror.

The irradiation light generation unit 30 of the present embodiment further includes a mirror 39a in addition to the above-described configuration. The mirror 39a bends the optical axis of the irradiation light L1 to optically couple the optical scanner 35 and the beam splitter 14 of the optical irradiation unit 10. The irradiation light generation unit 30 may include a component (an optical detector or the like) for detecting light to be detected from the biological object B and generating an image.

If a distance between the objective lens 12 and the spatial light modulator 33 is long, at least one 4f optical system may be provided on the optical axes of the irradiation light L1 and light to be detected L2. As an example, two 4f optical systems 51 and 52 are illustrated in FIG. 1. The 4f optical systems 51 and 52 have a function of transferring a wavefront of the irradiation light L1 generated in the spatial light modulator 33 to a rear side focus of the objective lens 12. The 4f optical system may include a telecentric relay optical system. Further, it is possible to omit the 4f optical system if the objective lens 12 is extremely close to the spatial light modulator 33.

The control unit 40 includes a processor. The control unit 40 controls the optical irradiation unit 10, the shape measurement unit 20, and the irradiation light generation unit 30. For example, the control unit 40 controls a position in the optical axis direction of the objective lens 12 using the objective lens moving mechanism 13 in the optical irradiation unit 10. Further, the control unit 40 moves the biological object table 11 that supports the biological object B in a direction crossing the optical axis direction. Further, the control unit 40 performs control of the coherent light source 21, the detector 24, and the reference light mirror 23 of the shape measurement unit 20. Further, the control unit 40 controls the laser light source 31, the spatial light modulator 33, and the optical scanner 35 of the irradiation light generation unit 30. The control unit 40 of this embodiment includes an input device 41 such as a mouse or a keyboard, and a computer 43.

Further, the control unit 40 constitutes a portion of the shape acquisition unit in this embodiment. The control unit 40 is electrically coupled to the detector 24 of the shape measurement unit 20. The control unit 40 receives the detection signal S1 that is output from the detector 24 of the shape measurement unit 20. The control unit 40 acquires information on the surface shape of the biological object B using a method using a Fourier transform or a $\lambda/4$ phase-shifting interferometry on the basis of the detection signal S1. Further, the control unit 40 is a hologram generation unit in the embodiment. The control unit 40 generates aberration correction hologram data for correcting aberration caused by the surface shape of the biological object B on the basis of the obtained information. The aberration correction hologram data is provided to the spatial light modulator 33. The control unit 40 may realize a function of controlling the respective units, a function as the shape acquisition unit, and a function as the hologram generation unit, using the same processor or may realize the functions using different processors.

Figure 2:
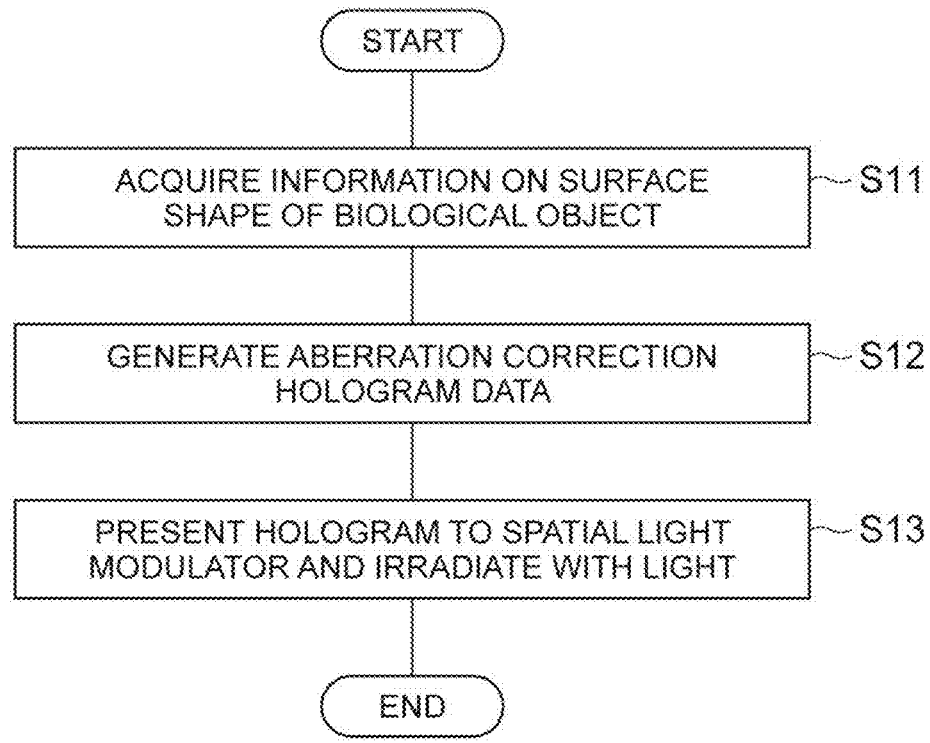
FIG. 2 is a flowchart illustrating an operation of a photostimulation apparatus.

FIG. 2 is a flowchart illustrating an operation of the photostimulation apparatus 1A described above. An photostimulation method according to this embodiment will be described with reference to FIG. 2.

First, the biological object B is placed on the biological object table 11. Then, the light L3 is output from the light source 21 of the shape measurement unit 20, and the detector 24 detects the interference light L4 of the reflected light from the surface of the biological object B and the reference light L31. Thus, an interference pattern is observed on the surface of the biological object B. In the control unit 40, information on the surface shape of the biological object B is acquired on the basis of the interference pattern (shape acquisition step S11).

Subsequently, aberration correction hologram data for correcting the aberration caused by the surface shape of the biological object B is generated by the control unit 40 on the basis of the information acquired in the shape acquisition step S11 (hologram generation step S12). Subsequently, the hologram based on the aberration correction hologram data is presented to the spatial light modulator 33. The light L5 emitted from the laser light source 31 is modulated by the spatial light modulator 33, and the biological object B is irradiated with the irradiation light L1 after modulation (light irradiation step S13). In the present embodiment, the light irradiation step S13 is performed repeatedly while the optical scanner 35 scans the irradiation light L1.

Effects obtained by the photostimulation apparatus 1A and the image acquiring method having the above configuration of this embodiment will be described. In many cases, the surface of the biological object B is not flat. Therefore, an aberration caused by the surface shape of the biological object B occurs. When a numerical aperture (NA) of the objective lens 12 is small or observation is performed at a shallow position in the biological object B, an influence thereof is less, but when the numerical aperture (NA) is great or the observation is performed at a deep position, the influence cannot be neglected. There is a problem in that a condensing intensity of the irradiation light L1 at the desired irradiation position inside the biological object B becomes weak or a condensing shape spreads when the irradiation light L1 is under an influence of such an aberration. Thus, there is a problem in that it is difficult to perform photostimulation limited at the desired irradiation position or the like.

Figure 3:
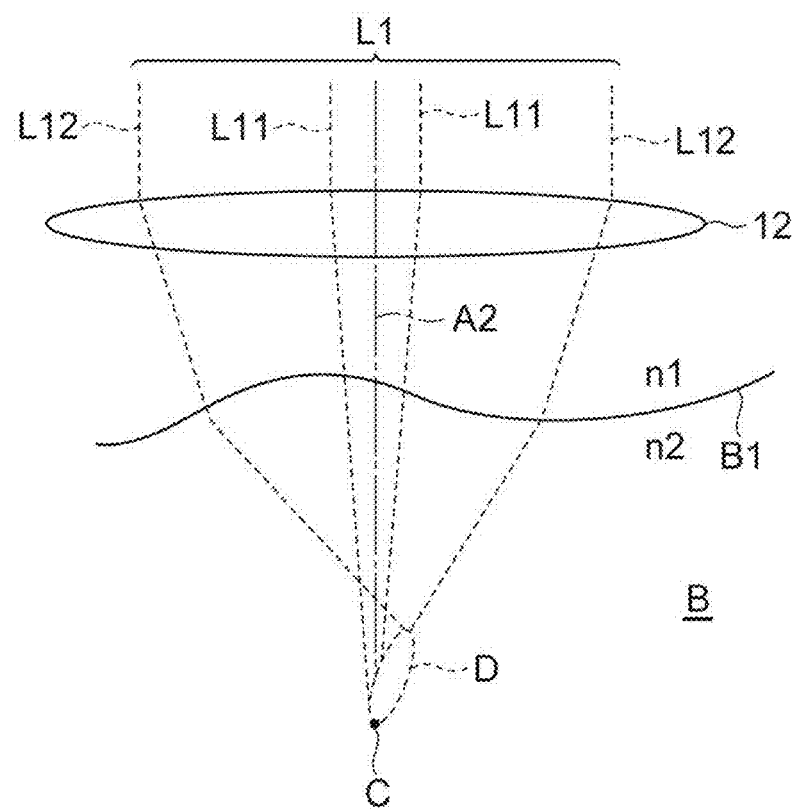
FIG. 3 is a diagram schematically illustrating a state of generation of an aberration.

FIG. 3 is a diagram schematically illustrating a state of occurrence of an aberration. In FIG. 3, a curve B1 represents a boundary between the surface of the biological object B, that is, the biological object B and outside thereof. It is assumed that a refractive index outside of the biological object B is n1 and a refractive index of the inside of the biological object B is n2 ($\neq$n1). The irradiation light L1 is condensed on the inside (directly under the surface) of the biological object B by the objective lens 12. In this case, light L11 that passes through the vicinity of an optical axis A2 of the objective lens 12 in the irradiation light L1 goes straight toward the condensing point C under almost no influence from the surface shape of the biological object B. On the other hand, light L12 passing through a position apart from the optical axis A2 of the objective lens 12 in the irradiation light L1 is refracted under the influence of the surface shape of the biological object B and deviates from the condensing point C. Due to this phenomenon, a condensing intensity of the irradiation light L1 inside the biological object B becomes weak and a condensing image D spreads.

In the photostimulation apparatus 1A and the photostimulation method of this embodiment, information on the surface shape of the biological object B is acquired. On the basis of the information, aberration correction hologram data for correcting an aberration is generated. Further, the irradiation light L1 is modulated by a hologram based on the data. Thus, since the aberration caused by the surface shape of the biological object B is preferably corrected, it is possible to suppress a decrease in the condensing intensity of the irradiation light L1 inside the biological object B and spreading of the condensing image D.

As in the present embodiment, information about a shape with a refractive index difference acquired in the shape measurement unit 20 and the shape acquisition step may include the surface shape of the biological object B. According to the photostimulation apparatus 1A and the photostimulation method described above, for example, in this case, it is possible to preferably suppress a decrease in condensing light intensity of the irradiation light L1 inside the biological object B and spreading of a condensing shape.

Figure 4:
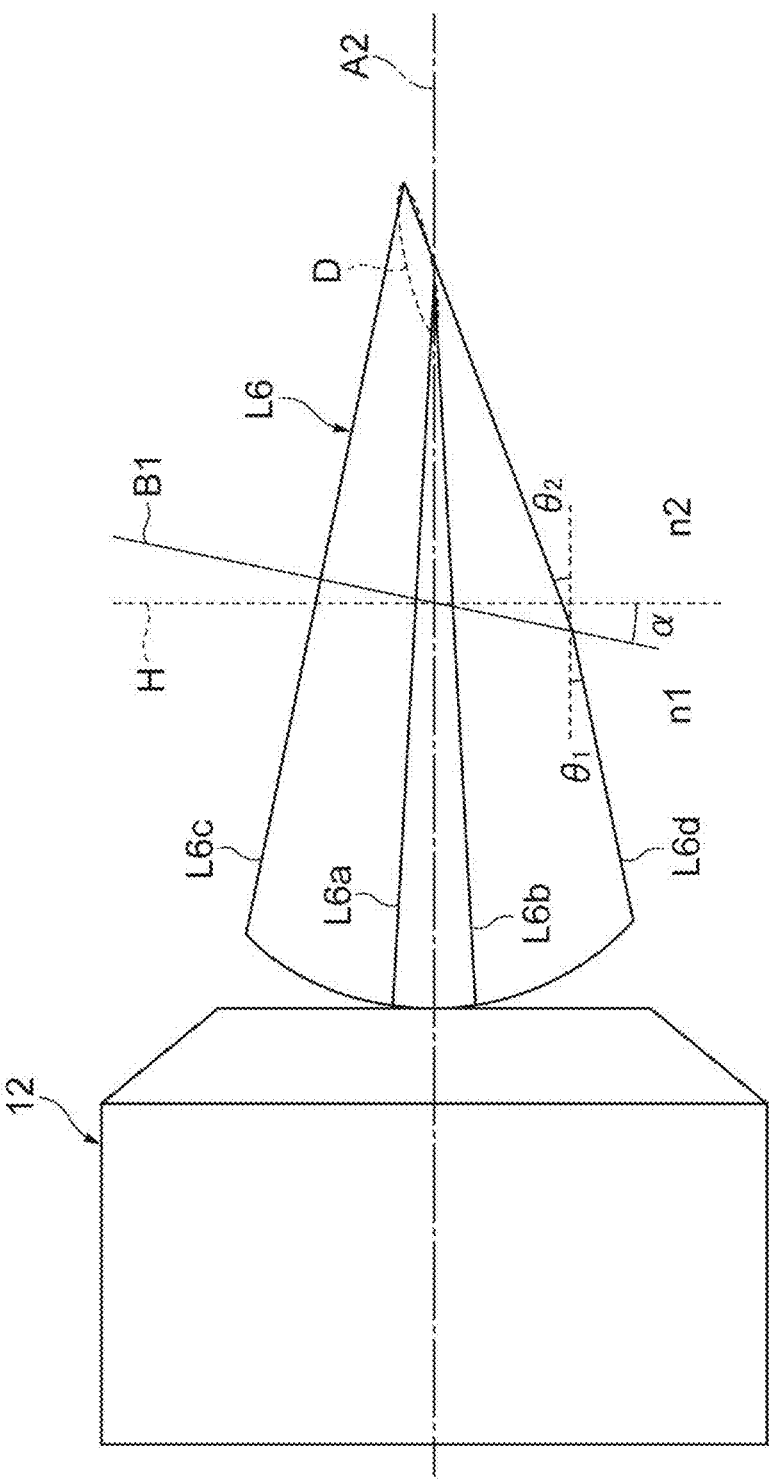
FIG. 4 conceptually illustrates a state of irradiation light when a boundary between a biological object and outside thereof is inclined from a plane perpendicular to an optical axis in a case in which irradiation light that is plane waves not subjected to aberration correction is condensed by an objective lens.

Here, a method of designing the aberration correction hologram will be described in detail. FIG. 4 conceptually illustrates a state of irradiation light L6 when a boundary B1 between the biological object B and outside thereof is inclined by an angle α from a plane H perpendicular to the optical axis A2 in a case in which the irradiation light L6 that is plane waves not subjected to the aberration correction is condensed by the objective lens 12. Here, lights L6a and L6b in FIG. 4 are rays passing through the vicinity of a center of the objective lens 12 and are referred to as paraxial rays. Further, lights L6c and L6d in FIG. 4 are rays passing through the vicinity of an edge of the objective lens 12, and are referred to as outer peripheral rays.

When the rays pass through a boundary between the biological object B and outside thereof, a relationship between an incidence angle $\theta_1$ and an output angle $\theta_2$ of the rays with respect to the boundary B1 is obtained using Snell's law expressed by the following Equation (1).

[Math. 1]

$$n_1 \sin(\theta_1 \pm \alpha) = n_2 \sin(\theta_2 \pm \alpha) \quad (1)$$

Since the incidence angle is small for the paraxial rays, the amount of change in the incidence angle and the output angle is small. On the other hand, since the incidence angle is large for the outer peripheral rays, the amount of change in the incidence angle and the output angle is large. Further, since the boundary B1 is inclined with respect to a plane perpendicular to the optical axis A2, the paraxial rays and the outer peripheral rays do not overlap on the optical axis. Accordingly, various aberrations occur and, as a result, the condensing image becomes a distorted image that is different from a diffraction limit image.

Figure 5:
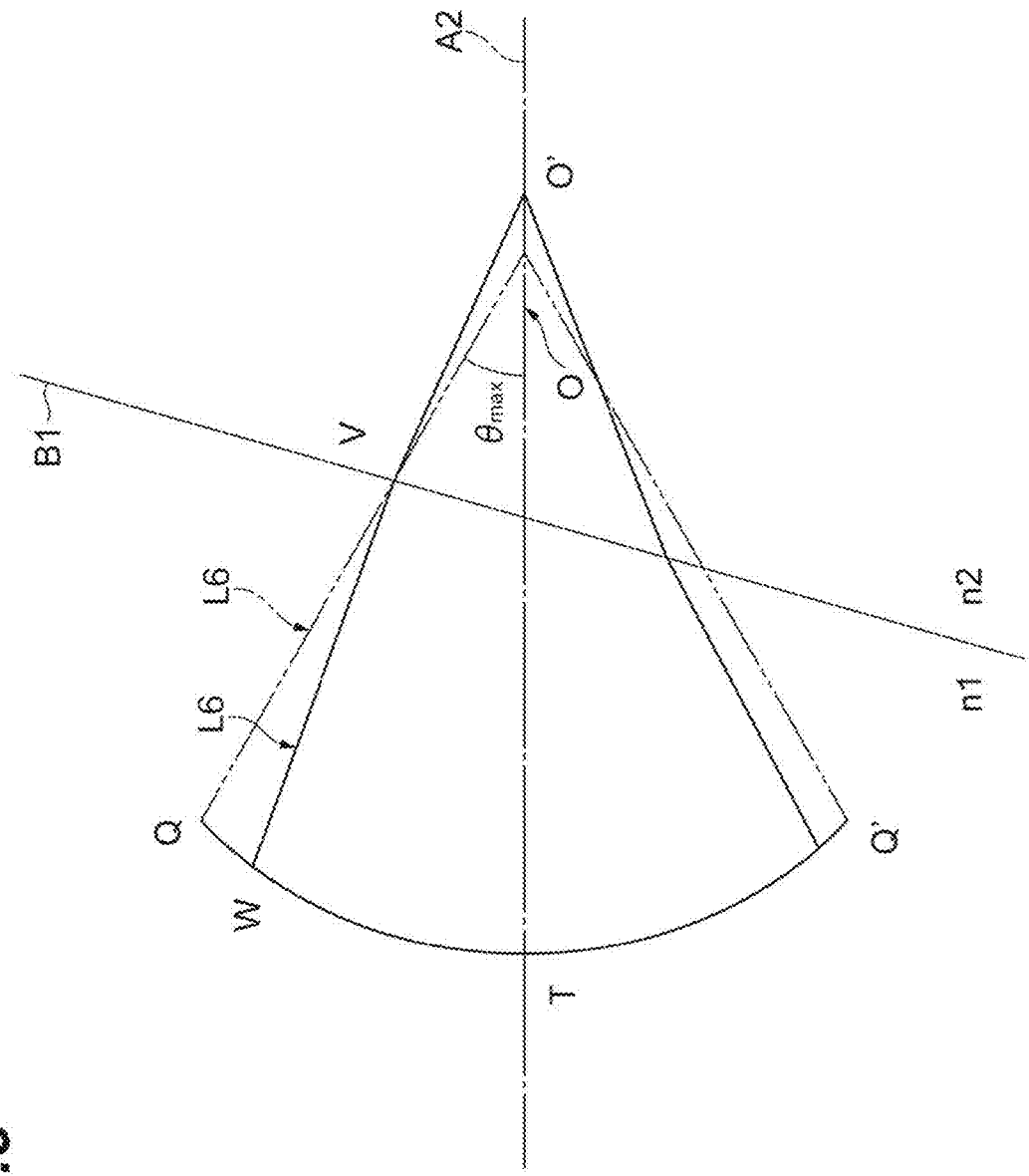
FIG. 5 is a diagram illustrating a method of calculating a wavefront for concentrating rays on any point on an optical axis.

FIG. 5 is a diagram illustrating a method of calculating a wavefront so that rays are concentrated on any point O' on the optical axis A2. An arc Q, Q' is a wavefront after the plane waves pass through the objective lens 12 with a focal length f and, for example, is a spherical crown with a certain radius. If there is no biological object B, the irradiation light L6A is condensed on another point O on the optical axis A2, as indicated by a two-dot chain line in FIG. 5. Here, an angle $\theta_{max}$ between a line segment OQ (or OQ') and a line segment OT is expressed by the following Equation (2). Here, NA is a numerical aperture of the objective lens 12. Further, T is an intersection of the arc Q, Q' and the optical axis A2.

[Math. 2]

$$\theta_{max} = \sin^{-1}(NA/n1) \qquad (2)$$

The rays of the irradiation light L6A are input to the objective lens 12 from the left on the paper, surface, and proceed to the right of the paper surface as convergent light. This direction is defined as a positive propagation direction. For example, an optical path from the point O' to a point W on an arc QQ' via a point V on the boundary B1 is obtained through backpropagation. In this embodiment, for example, the optical path is obtained through backpropagation using a method such as backward ray tracing, wavefront propagation, and electromagnetic field analysis to be described below.

<Backward Ray Tracing>

In this embodiment, in a previous step of optical path calculation, a structure of the biological object B is recognized using interference measurement. Therefore, a refractive index distribution in the biological object B is estimated from the structure of the biological object B, and the boundary B1 of the refractive index is obtained. The boundary B1 of this refractive index is subjected to polynomial approximation or map conversion so that the position can be specified.

Then, a path along which rays reach a point W on the arc QQ' from the point O' via the point V on the refractive index boundary B1' and an optical path length are determined. If the rays from the point O' propagate back, the rays reach the point V on the refractive index boundary B1. The point V is obtained by the above-described polynomial approximation or the like. The rays are refracted at the point V using Snell's law due to a refractive index difference before and after the boundary B1. In this embodiment, since the boundary B1 that is not uniform (that has irregular unevenness) is assumed, a three-dimensional Snell's law using a vector and a cross product as shown in Equation (3) below is applied.

[Math. 3]

$$n_1 \cdot m \times VW = n_2 \cdot m \times O'V \qquad (3)$$

Here, × in Equation (3) denotes a cross product. Further, in Equation (3), m is a normal vector at the point V, and VW and O'V are direction vectors after boundary passage and before boundary passage. After refraction, the rays propagate back again to the point W on the arc QQ'. Thus, the optical path length L is calculated by examining the optical path from the point O' to the point W. The optical path length L is determined using, for example, Equation (4) below.

[Math. 4]

$$L = n_1 |VW| + n_2 |O'V| \qquad (4)$$

The above calculation is performed on a plurality of rays to obtain the optical path lengths of all the rays reaching the spherical crown. A phase difference is obtained through the optical path difference from the optical path length, and a pattern for eliminating this phase difference becomes an aberration correction pattern, that is, aberration correction hologram data. In practice, since there are a plurality of boundaries B1 of the refractive index, the rays may be refracted at each boundary B1 of the refractive index and traced. In this case, Equation (4) is changed.

<Wavefront Propagation>

Using Fresnel diffraction, Fresnel-Kirchhoff diffraction, or the like, rays gradually propagate back from a position at which the rays condense (point O') to the objective lens 12. In this case, the calculation is performed by adding the boundary B1 of the refractive index to the propagation. This method may be combined with the backward ray tracing described above or electromagnetic field analysis to be described below. For example, reverse ray tracing may be performed on a portion other than the boundary B1 of the refractive index, and wavefront propagation may be performed on a portion including the boundary B1 of the refractive index. Thus, it is possible to reduce a calculation load.

<Electromagnetic Field Analysis>

Using a Finite-Difference Time-Domain (FDTD) method or a Rigorous Coupled-Wave Analysis (RCWA) method, analysis is performed from a point O' at which condensing is desired to the objective lens 12. In this case, the boundary B1 of the refractive index is added to boundary conditions. This method may be combined with the above-described backward ray tracing or wavefront propagation.

Figure 6:
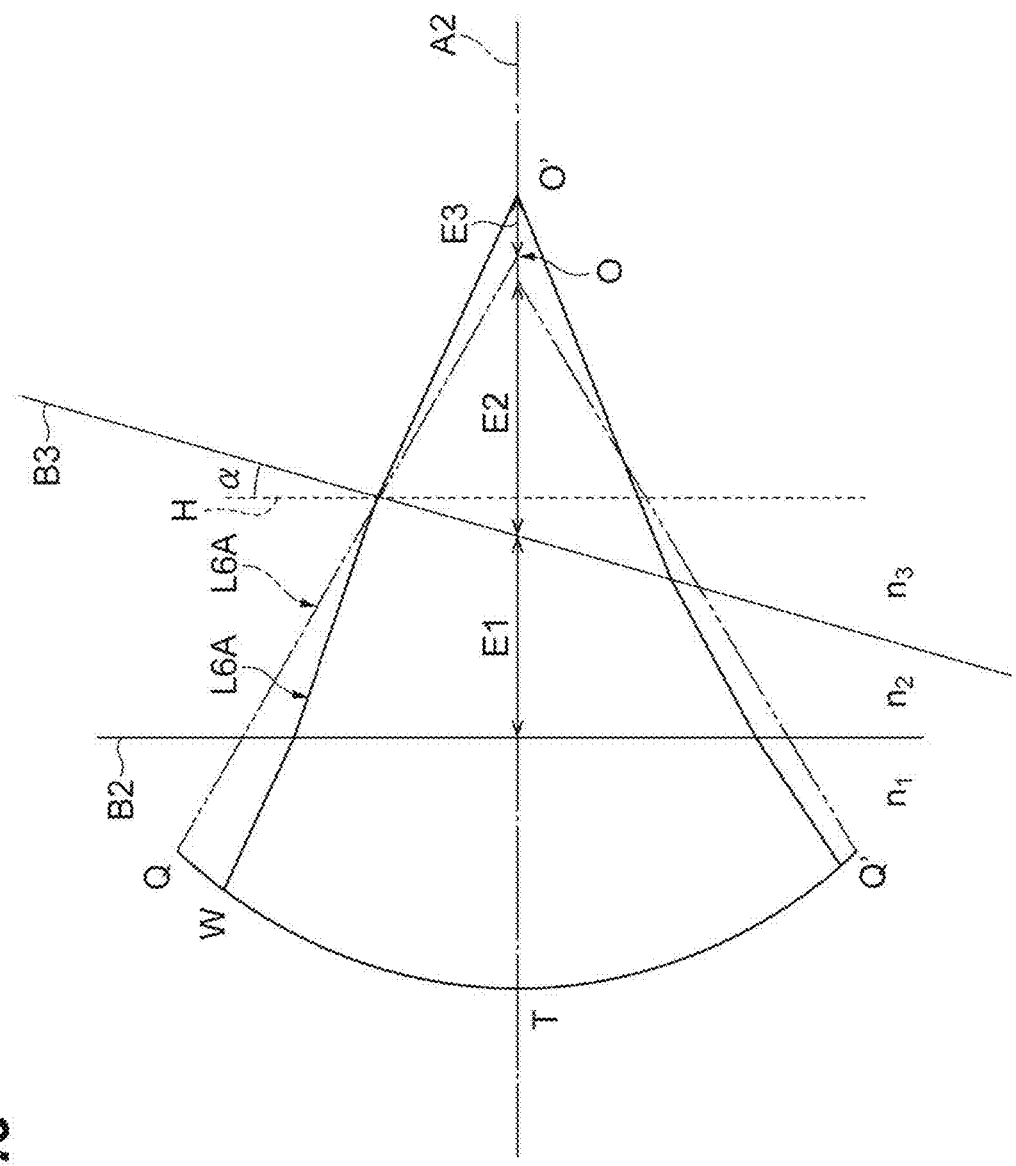
FIG. 6 schematically illustrates a case in which there is a boundary between two refractive indexes.

Conversely propagation analysis using each method described above is applicable even when there are two boundaries of the refractive index. FIG. 6 schematically illustrates a case where there are two refractive index boundaries B2 and B3. The boundary B2 is assumed to be perpendicular to the optical axis. Further, an angle between a plane H perpendicular to the optical axis A2 and the boundary B3 is $\alpha$. The refractive index outside of the boundary B2 is n1, the refractive index between the boundary B2 and the boundary B3 is n2, and the refractive index inside of the boundary B3 is n3.

Figure 7:
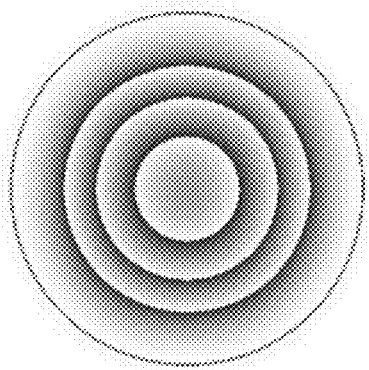
FIGS. 7(a) and 7(b) are diagrams illustrating a wavefront obtained using backpropagation analysis, in which a phase is indicated by shading.
Figure 7:
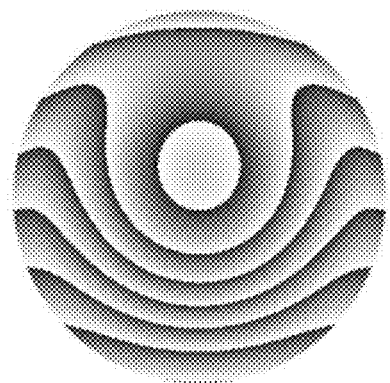

FIGS. 7(a) and 7(b) are diagrams illustrating the wavefront obtained using the backpropagation analysis in such a case, and a phase is indicated by shading. FIG. 7 is represented using a technology called phase folding. FIG. 7(a) illustrates a wavefront obtained when $\alpha = 0°$. Further, FIG. 7(b) illustrates a wavefront obtained when $\alpha = 0.3°$. In the calculation of the wavefronts, n1=1, n2=1.33, and n3=1.38. In this case, n1 simulates air, n2 simulates water, n3 simulates a cell. It is assumed that there is a cover glass at the boundary B2 between n1 and n2, but an aberration caused by the cover glass is corrected using a glass correction function of the objective lens 12. A region sandwiched between the boundary B2 and the boundary B3 on the optical axis (that is, a region sandwiched between the cover glass and the cell) is filled with, for example, phosphate buffered saline. A distance E1 between the boundary B2 and the boundary B3 on the optical axis is, for example, 30 μm. Further, a magnification of the objective lens 12 is 40, a numerical aperture (NA) is 0.75, a distance E2 between the point O and the boundary B3 on the optical axis is 300 μm, and a distance E3 between the point O and the point O' is 80 μm. In the above conditions, a coma aberration and an astigmatism aberration are included in the wavefront, in addition to the spherical aberration. As illustrated in FIG. 7, a wavefront required for the irradiation light is preferably obtained using the above-described backpropagation analysis. An aberration correction hologram is preferably obtained on the basis of the wavefront.

As a method of correcting the aberration caused by the surface shape of the biological object B, for example, a method of combining a phase modulator (mainly, a deformable mirror) with a wavefront measurement device (a Shack-Hartmann sensor) and embedding fluorescent beads with a known size or shape at a particular position inside the biological object B can be considered. In this method, excitation light and fluorescence from the fluorescent beads are both under an influence of aberration. Therefore, the aberration is measured by measuring a fluorescence intensity distribution using the wavefront measurement device. A hologram for correcting the aberration is presented to the phase modulator. In this case, the fluorescent beads are used as reference information. However, in such a method, it is necessary for fluorescent beads to be embedded by surgery, and this method is not applicable in a case in which it is difficult to embed the fluorescent beads or a state of the biological object B being changed due to the embedded fluorescent beads. On the other hand, according to the method of this embodiment, it is not necessary to embed the fluorescent beads.

Further, a method of obtaining an aberration correction hologram by trial and error by presenting a plurality of holograms by which an aberration is assumed to be reduced to a spatial light modulator, scanning the irradiation light modulated by the spatial light modulator, and selecting a hologram by which luminance or resolution of an obtained image is improved may be considered. However, such a method takes a long time to repeat an experiment and design. Further, the obtained aberration correction hologram is likely to be an approximate solution, and accuracy is suppressed to be low. On the other hand, in the method of this embodiment, since the calculation of the aberration correction hologram data is all performed in the computer 43, it is possible to shorten the required time as compared with the method with trial and error of an operator. Further, in the method of this embodiment, since the computer 43 generates the aberration correction hologram data on the basis of the information on the surface shape acquired in the shape measurement unit 20, it is possible to enhance accuracy of the aberration correction.

The hologram presented on the spatial light modulator 33 may not be the aberration correction hologram. For example, the hologram may be a hologram obtained by superimposing another hologram such as a hologram for controlling a condensed light shape or a condensed light position of the irradiation light L1 to be radiated toward the biological object B and the aberration correction hologram.

Second Embodiment

In the first embodiment, an example of the surface shape of the biological object B has been described as a shape with the refractive index difference due to a factor of occurrence of the aberrations, but an example of an internal structure directly under a surface of the biological object B is additionally included as a shape with a refractive index difference. Hereinafter, this case will be described in detail.

Even when the biological object B is irradiated with irradiation light with a certain light intensity, an intensity per unit volume of the irradiation light is different between a deep position and a shallow position of the biological object B. This is due to scattering and an aberration of the irradiation light caused by an internal structure of the biological object B. One cause of occurrence of the scattering or the aberration is a change in the optical path caused by a refractive index difference between organs constituting, macroscopically, a structure of a blood vessel or the like and, microscopically, a cell. In particular, at a deep position in the biological object B, the optical path is changed due to the internal structure, and a condensing shape of the irradiation light is greatly changed. Thus, a condensed light intensity of the irradiation light is weakened at a desired irradiation position inside the biological object B or a condensed light range spreads. Thus, it is difficult to perform photostimulation limited to the desired irradiation position.

Therefore, in this embodiment, an internal structure with a refractive index difference directly under the surface of the biological object B is measured, and a hologram including an aberration correction hologram for correcting an aberration caused by the internal structure is presented to the spatial light modulator 33. Thus, a decrease in condensing intensity of the irradiation light L1 and spreading of the condensed light range are suppressed.

Figure 8:
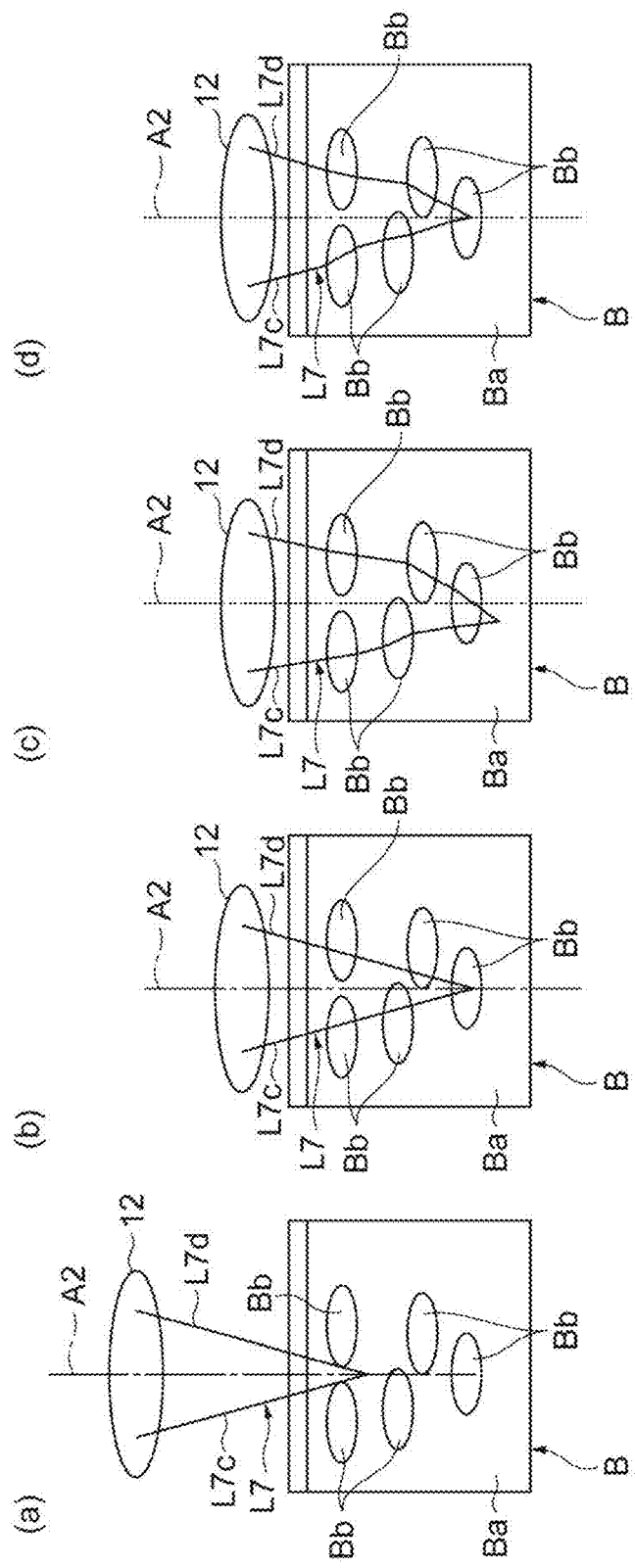
FIGS. 8(a) to 8(d) are diagrams when a biological object is viewed from the side, and conceptually illustrate a state in which irradiation light is condensed while passing through an internal structure including media with different refractive indexes.

FIGS. 8(a) to 8(d) are diagrams when the biological object B is viewed from the side, and schematically illustrate a state in which irradiation light is condensed while passing through an inner structure including media Ba and Bb with different refractive indexes. FIGS. 8(a) and 8(b) illustrate a state of condensing of irradiation light L7 when no aberration is assumed, and the irradiation light L7 is condensed in a shallow position and a deep position in the biological object B. As illustrated in FIG. 8(a), when the irradiation light L7 is condensed in the shallow position, the boundary of the refractive index present on the optical path is relatively small. On the other hand, as illustrated in FIG. 8(b), when the irradiation light L7 is condensed in the deep position, the boundary of the refractive index present on the optical path increases. Therefore, in such a case, the irradiation light is actually influenced by the internal structure of the biological object B, as illustrated in FIG. 8(c). When the aberration correction is not performed as in FIG. 8(c), rays L7c and L7d near a lens outer peripheral portion are refracted under an influence of the internal structure. On the other hand, since a refraction angle of rays near the optical axis A2 is small, the rays near the optical axis A2 are less affected by the internal structure. As a result, a focus position of the rays near the optical axis A2 is different from a focus position of the rays L7c and L7d, and an aberration occurs. FIG. 8(d) illustrates a case in which such an aberration has been corrected. By correcting the wavefront of the irradiation light L7 in consideration of the refractive index distribution of the internal structure, the focus position of the rays near the optical axis A2 matches the focus position of the rays L7c and L7d, and condensing of the irradiation light L7 can be achieved at high density.

Figure 9:
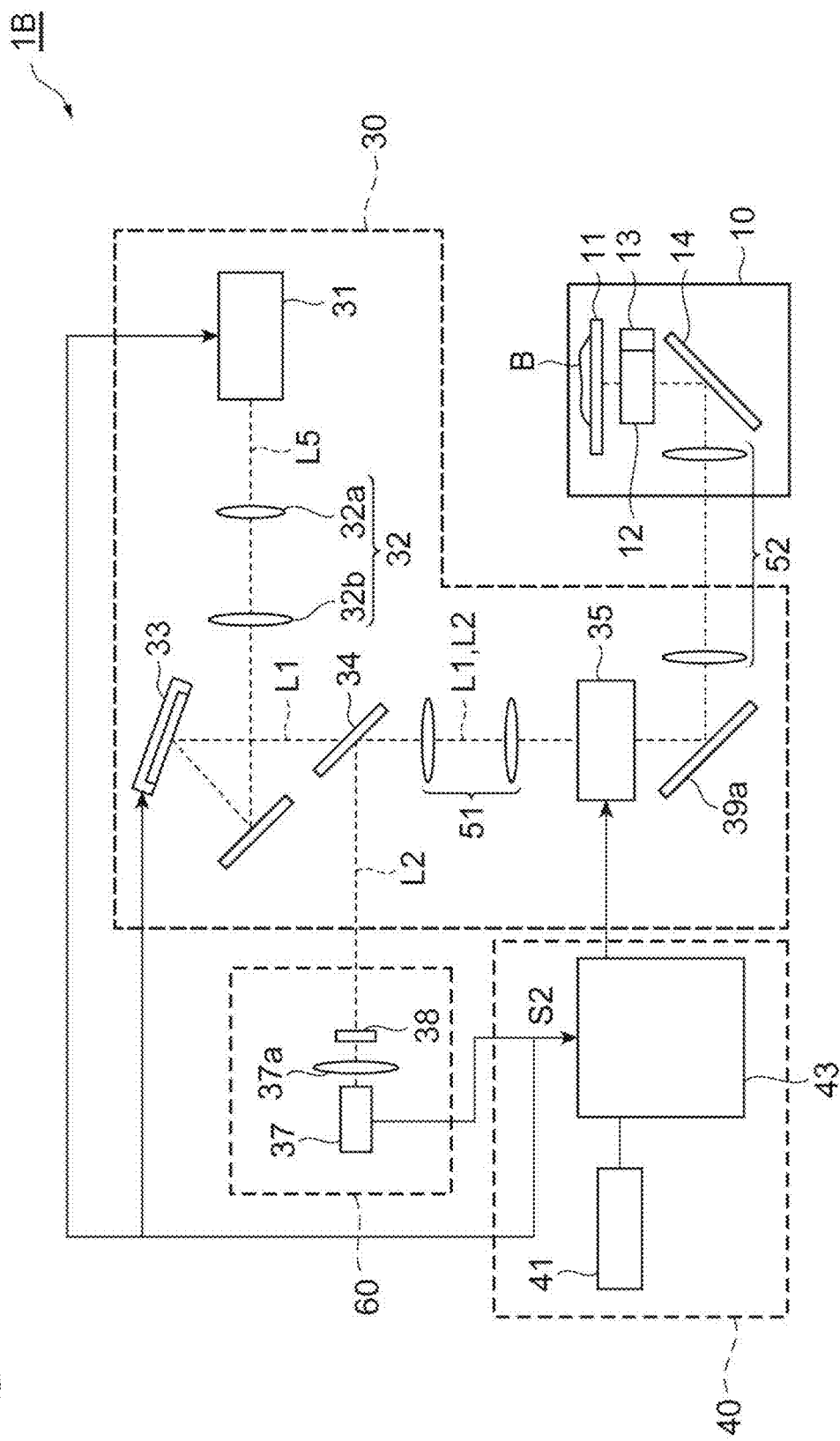
FIG. 9 is a diagram illustrating a configuration of a photostimulation apparatus of a second embodiment.

FIG. 9 is a diagram illustrating a configuration of a photostimulation apparatus 1B of this embodiment. As illustrated in FIG. 9, the photostimulation apparatus 1B does not include the shape measurement unit 20 as compared with the photostimulation apparatus 1A of the above-described first embodiment, and includes a dichroic mirror 34, a detector 37, and a filter 38 in place thereof. The detector 37 and the filter 38 constitute a shape measurement unit 60 which is a shape acquisition unit in the present embodiment. The shape measurement unit 60 includes the detector 37 and is optically coupled to the objective lens 12.

The dichroic mirror 34 transmits one of the irradiation light L1 from the spatial light modulator 33 and the light to be detected L2 from the optical irradiation unit 10 and reflects the other. In the example illustrated in FIG. 1, the dichroic mirror 34 transmits the irradiation light L1 and reflects the light to be detected L2. Here, the light to be detected L2 is light generated in the biological object B by the irradiation light L1 and is fluorescent light excited by, for example, reflected light of the irradiation light L1, harmonic waves of the irradiation light L1, or the irradiation light L1. The light to be detected L2 is collected by the objective lens 12 and reaches the dichroic mirror 34 through the 4f optical system 52, the reflecting mirror 39a, the optical scanner 35, and the 4f optical system 51.

The detector 37 detects a light intensity of the light to be detected L2 output from the biological object B via the objective lens 12 and outputs a detection signal S2. The light to be detected L2 is scanned by the optical scanner 35, reflected by the dichroic mirror 34, and detected by the detector 37. The detector 37 may be a point sensor such as a photomultiplier tube (PMT), a photodiode, or an avalanche photodiode. Alternatively, the detector 37 may be an area image sensor such as a CCD image sensor, a CMOS image sensor, a multi-anode PMT, or a photodiode array. A condensing lens 37a may be arranged directly under the detector 37.

The filter 38 is arranged on an optical axis between the dichroic mirror 34 and the detector 37. The filter 38 cuts a wavelength of the irradiation light L1, a wavelength of fluorescent light unnecessary in observation, or the like from light input to the detector 37. The filter 38 may be arranged in either of a previous stage and a subsequent stage of the condensing lens 37a.

As described above, the photostimulation apparatus 1B of the present embodiment does not include the shape measurement unit 20, and includes a shape measurement unit 60 in place thereof. The shape measurement unit 60 is a shape acquisition unit which acquires information about an internal structure directly under the surface of the biological object B. In the present embodiment, the objective lens 12 is moved in an optical axis direction and the computer 43 acquires information about the internal structure of the biological object B on the basis of the obtained detection signal S2.

With the configuration of this embodiment, it is possible to acquire information on the internal structure directly under the surface of the biological object B. That is, when a suitable fluorescent material is used, information on the internal structure of the biological object B is included in the obtained fluorescence image. Therefore, a distance between the objective lens 12 and the biological object B is sequentially changed using the objective lens moving mechanism 13. When the irradiation light (excitation light) L1 is condensed at a deep position inside the biological object B, fluorescence (including autofluorescence) is emitted from a structure inside the biological object B present on the optical path of the irradiation light (excitation light) L1. Accordingly, it is possible to recognize a refractive index distribution of the biological object B by acquiring the fluorescence intensity while setting a focus position shallower. It is possible to reduce an influence of an aberration by presenting the aberration correction hologram taking the recognized refractive index distribution into account to the spatial light modulator 33. In this embodiment, the biological object B may be a sample that emits fluorescence from a specific portion due to a fluorescent dye, a fluorescent protein, autofluorescence, or Second Harmonic Generation (SHG), or the like. Further, in the following description, the operation for measurement of the internal structure as described above using the objective lens moving mechanism 13, the laser light source 31, the optical scanner 35, and the detector 37 is referred to as pre-scan.

In the photostimulation apparatus 1B, scanning is performed by the optical scanner 35 (for example, an XY galvanometer) in order to observe the fluorescent image within a plane perpendicular to the optical axis. Information within a plurality of planes with different depths is obtained through a movement of the objective lens 12 or the biological object table 11 in the optical axis direction. Finally, three-dimensional information is constructed by combining the information.

Further, the shape acquisition unit may measure the refractive index distribution using light sheet light used for fluorescence observation of a single photon, ultrasound, or the like, in place of the above configuration or together with the above configuration. Thus, it is possible to recognize a rough structure before observation in advance and preferably design an aberration correction hologram for correcting an aberration caused by the structure.

Figure 10:
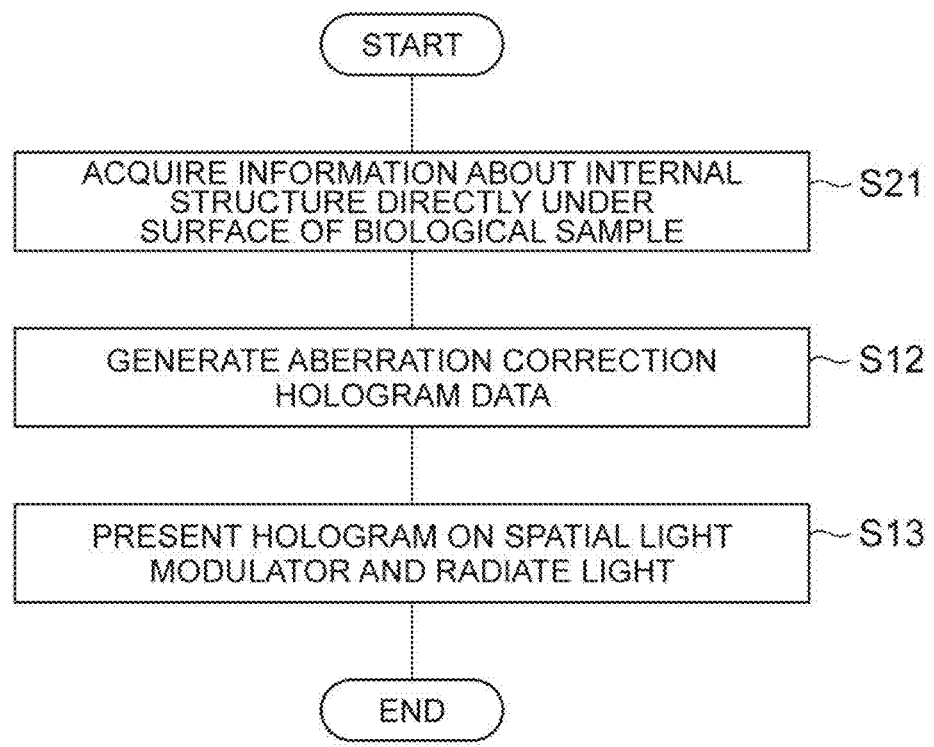
FIG. 10 is a flowchart illustrating an operation of a photostimulation apparatus and an photostimulation method according to this embodiment.

FIG. 10 is a flowchart illustrating an operation of the photostimulation apparatus 1B described above, and an photostimulation method according to this embodiment. First, the biological object B is placed on the biological object table 11. Then, a focus position is gradually moved from a shallow position in the biological object B to a deep position while moving the objective lens 12 in an optical axis direction. At the same time, the detector 37 detects light to be detected L2 (fluorescent light) from an internal structure directly under a surface of the biological object B by outputting the light L5 from the laser light source 31 and condensing the irradiation light L1 directly under the surface of the biological object B. In this case, the aberration correction is not performed by the spatial light modulator 33. Thus, a change in fluorescence in a depth direction caused by the internal structure directly under the surface of the biological object B is detected. This operation is performed repeatedly while moving the optical axis of the irradiation light L1 using the optical scanner 35. Accordingly, three-dimensional information on the internal structure of the biological object B is constructed. A refractive index distribution is estimated from the constructed three-dimensional information (shape acquisition step S21).

Thereafter, the hologram generation step S12, and the light irradiation step S13 are performed, similar to the first embodiment. In the observations at a deep position, since the irradiation light L1 passes through a portion or all of the estimated refractive index distribution, an aberration correction hologram may be generated so that an influence of the refractive index distribution on the irradiation light L1 passing through the refractive index distribution is reduced in the hologram generation step S12. In this embodiment, the aberration correction hologram is designed on the basis of a wavefront obtained through backpropagation using geometrical optics, wave optics, electromagnetic field analysis, or the like. The geometrical optics is, for example, backward ray tracing, the wave optics is, for example, Fresnel wavefront propagation or Fresnel Kirchhoff diffraction, and the electromagnetic field analysis is, for example, FDTD or RCWA.

Although the aberration correction hologram is generated on the basis of the surface shape of the biological object B in the first embodiment, and the aberration correction hologram is generated on the basis of the structure with a refractive index distribution directly under the surface of the biological object B in the second embodiment, the aberration correction hologram may be generated on the basis of both of the surface shape of the biological object B and the structure directly under the surface of the biological object B.

Further, although the shape acquisition unit of this embodiment acquires the information on the structure directly under the surface of the biological object B using fluorescence obtained by radiating the irradiation light L1, the shape acquisition unit may measure the refractive index distribution directly under the surface of the biological object B using ultrasound or may measure the refractive index distribution directly under the surface using a phase difference or a differential interference. Alternatively, the shape acquisition unit may change an angle of the optical axis or change a refractive index of an immersion liquid and estimate the refractive index distribution or a scattering degree directly under the surface from reflection, transmission, or the like. Accordingly, it is possible to estimate, particularly, the refractive index distribution in the surface of the biological object B. For example, when the angle of the optical axis is changed, the refractive index of the surface of the biological object B or the refractive index distribution inside the sample can be estimated from a Brewster angle or a relationship between the angle and a reflectance.

Effects obtained by the photostimulation apparatus 1B and the image acquiring method having the above configuration of this embodiment will be described. In the photostimulation apparatus 1B and the image acquiring method of this embodiment, the information on the internal structure directly under the surface of the biological object B is acquired. On the basis of this information, the aberration correction hologram data for correcting the aberration is generated. Further, the irradiation light L1 is modulated using the hologram based on the data. Thus, since the aberration caused by the internal structure directly under the surface of the biological object B is preferably corrected, it is possible to suppress a decrease in the condensing intensity of the irradiation light L1 and spreading of the condensing shape inside the biological object B.

As in the present embodiment, information about a shape with the refractive index difference obtained in the shape measurement unit 60 and the shape acquisition step may include a structure directly under the surface of the biological object B. According to the photostimulation apparatus 1B and the photostimulation method described above, for example, in this case, it is possible to preferably suppress a decrease in condensing intensity of the irradiation light L1 inside the biological object B and spreading of a condensing shape.

First Modification Example

Figure 11:
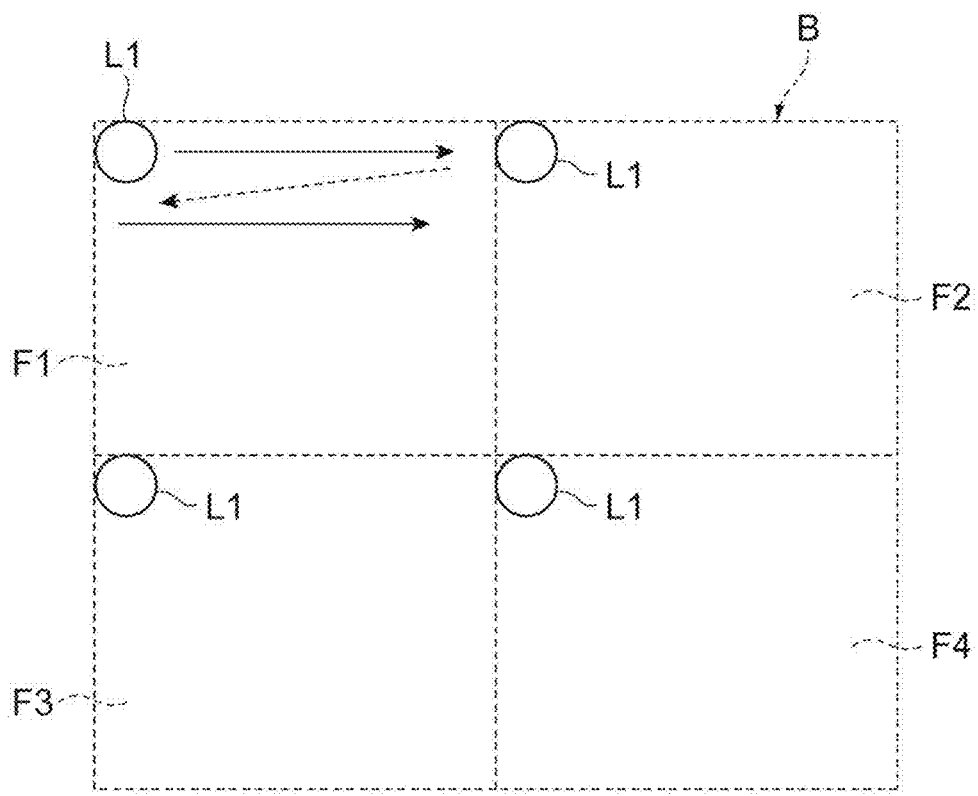
FIG. 11 is a diagram illustrating an operation of a first modification and is a diagram when a surface of a biological object is viewed in an optical axis direction.

FIG. 11 is a diagram illustrating an operation of a first modification example, and is a diagram when the surface of the biological object B is viewed in the optical axis direction. In the second embodiment, the shape acquisition unit may divide a surface of the biological object B into a plurality of regions F1 to F4 in a grid pattern as illustrated in FIG. 11 and perform scanning in small areas in parallel in the respective regions F1 to F4 (in the shape acquisition step). In this case, an individual aberration correction hologram is generated for each of the regions F1 to F4, and a hologram having effects of aberration correction and multi-point generation is presented to the spatial light modulator 33.

Figure 12:
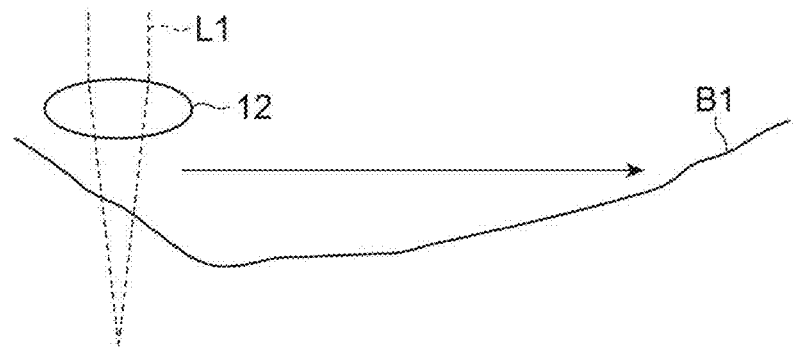
FIGS. 12(a) and 12(b) are diagrams illustrating a state of scanning of the first modification example.
Figure 12:
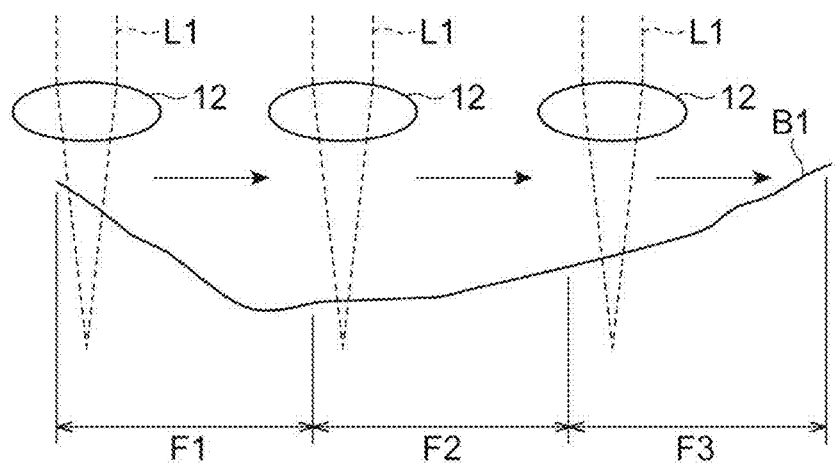

FIGS. 12(a) and 12(b) are diagrams illustrating examples of a boundary B1 at the outer side of the biological object B. Since a distance between the objective lens 12 and the boundary B1 and an internal structure directly under the surface of the biological object B greatly change when the irradiation light L1 scans a wide region as illustrated in FIG. 12(a), an aberration correction hologram may be switched midway. However, in this case, a loss of time is caused by a slow operation of the spatial light modulator. On the other hand, when a size of the scanning region is reduced through division into a plurality of regions F1 to F4 as illustrated in FIG. 12(b), it is not necessary to switch the aberration correction hologram, and high-accuracy and high-speed scanning are realized.

Second Modification Example

Figure 13:
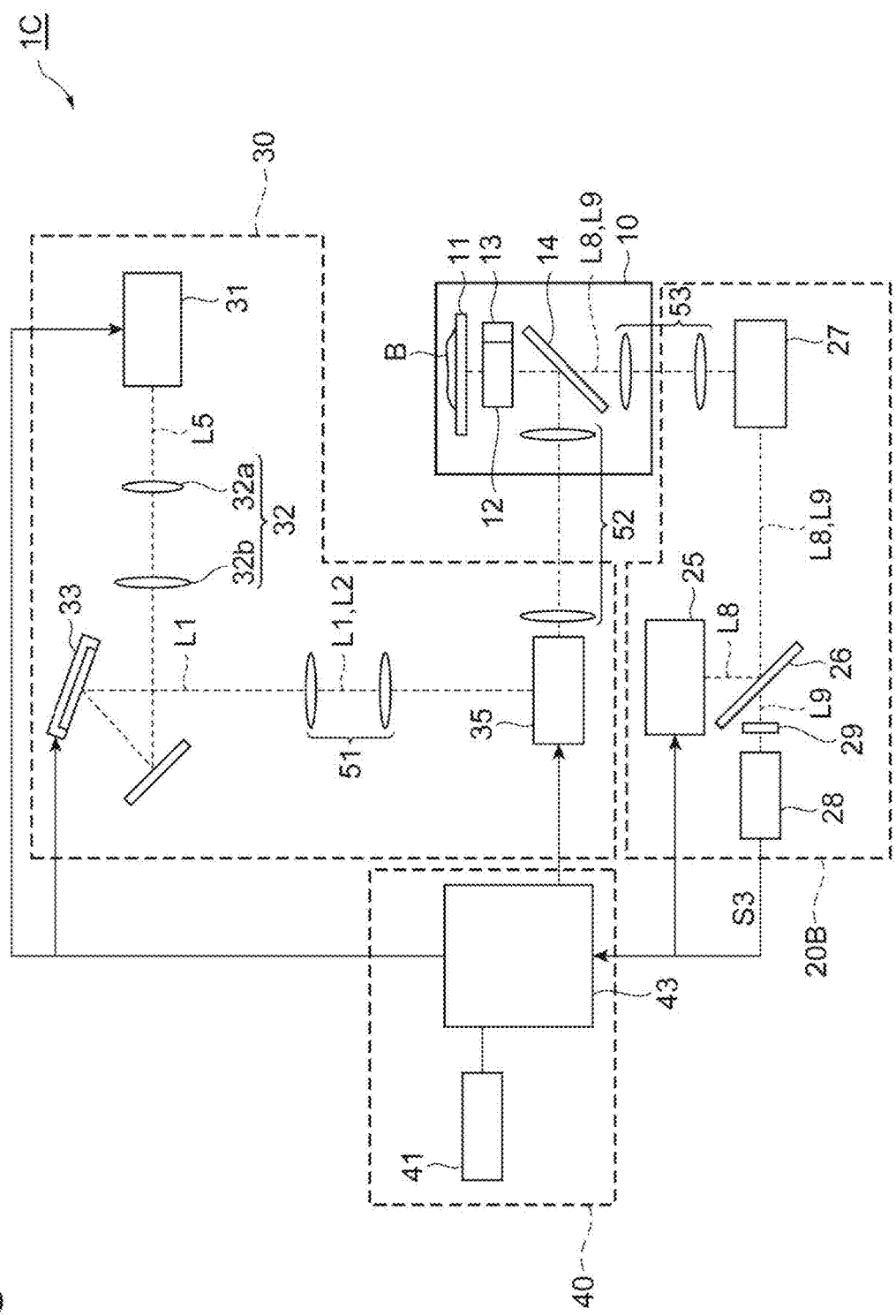
FIG. 13 is a diagram illustrating a configuration of a photostimulation apparatus according to a second modification example.

FIG. 13 is a diagram illustrating a configuration of a photostimulation apparatus 1C according to a second modification example. In the photostimulation apparatus 1C of this modification example, a shape measurement unit 20B constitutes the shape acquisition unit. The shape measurement unit 20B includes a light source 25, a dichroic mirror 26, an optical scanner 27, a detector 28, and a filter 29. The shape measurement unit 20B includes a detector 28 and is optically coupled to an objective lens 12.

The light source 25 outputs excitation light L8 with which a biological object B is irradiated. In this modification example, the biological object B may be a sample that emits fluorescence from a specific portion due to a fluorescent dye, a fluorescent protein, autofluorescence, SHG, or the like, similar to the second embodiment. Then, the excitation light L8 is light including a wavelength that excites the biological object B. The excitation light L8 may be light with the same wavelength as the light L5 output from the laser light source 31 or may be light with a wavelength different from that of the light L5 output from the laser light source 31.

The dichroic mirror 26 transmits one of the excitation light L8 from the light source 25 and fluorescence L9 from the optical irradiation unit 10, and reflects the other. In the example illustrated in FIG. 13, the dichroic mirror 26 reflects the excitation light L8 and transmits the fluorescence L9.

The optical scanner 27 scans an irradiation position of the excitation light L8 in the biological object B by moving an optical axis of the excitation light L8 within a plane perpendicular to the optical axis of the excitation light L8. The optical scanner 27 includes, for example, a galvanometer mirror, a resonant mirror, or a polygon mirror. The fluorescence L9 from the biological object B is detected through the optical scanner 27. Thus, it is possible to match the optical axis of the excitation light L8 with the optical axis of the fluorescence L9.

The detector 28 detects a light intensity of the fluorescence L9 output from the biological object B via the objective lens 12, and outputs a detection signal S3. The detector 28 may be a point sensor such as a PMT, a photodiode, or an avalanche photodiode. Alternatively, the detector 28 may be an area image sensor such as a CCD image sensor, a CMOS image sensor, a multi-anode PMT, or a photodiode array. A confocal effect may be imparted due to a pinhole disposed at a preceding stage from the detector 28.

The filter 29 is disposed on an optical axis between the dichroic mirror 26 and the detector 28. The filter 29 cuts a wavelength of the excitation light L8 and a wavelength of fluorescence or the like unnecessary for observation from the light that is input to the detector 28.

When a distance between the objective lens 12 and the light source 25 is long, at least one 4$f$ optical system may be provided on an optical axis of the excitation light L8 and the fluorescence L9. As an example, one 4$f$ optical system 53 is illustrated in FIG. 13. The 4$f$ optical system 53 is disposed on the optical axis between the optical scanner 27 and the beam splitter 14.

In this modification, first, the biological object B is placed on the biological object table 11. Then, a focus position is gradually moved from a shallow position in the biological object B to a deep position while moving the objective lens 12 in an optical axis direction. At the same time, the light L8 is output from the laser light source 25 and fluorescence L9 from the internal structure directly under the surface of the biological object B is detected in the detector 28. Thus, a change in the fluorescence in a depth direction caused by the internal structure directly under the surface of the biological object B is detected. This operation is repeatedly performed while moving the optical axis of the excitation light L8 using the optical scanner 27. Accordingly, three-dimensional information on the internal structure of the biological object B is constructed. A refractive index distribution is estimated from the constructed three-dimensional information. A subsequent operation is the same as in the second embodiment described above. When a wavelength of the excitation light L8 is included in wavelengths of the light L5 output from the laser light source 31, the functions of the light source 25 and the optical scanner 27 may be realized by the laser light source 31 and the optical scanner 35. In this case, the light source 25, the optical scanner 27, and the dichroic mirror 26 are not necessary.

Third Modification Example

In the second embodiment described above, pre-scan may be repeated a plurality of times, and in the second and subsequent pre-scans, an aberration of light L5 may be corrected by the spatial light modulator 33 on the basis of a previous pre-scan result. Thus, when the biological object B is irradiated with the light L5, it is possible to reduce an influence of an aberration caused by the internal structure of the biological object B, more accurately recognize a structure of the biological object B, and obtain a higher resolution image.

Specifically, in first pre-scan, the irradiation light L1 becomes plane waves since the aberration correction is not performed, but in second pre-scan, a wavefront for correcting the aberration is applied to the irradiation light L1. The aberration correction hologram is designed on the basis of a structure of the biological object B obtained by the second and subsequent pre-scans. Alternatively, rough aberration correction may be performed by the first pre-scan, and finer aberration correction may be performed by the second and subsequent pre-scans.

Fourth Modification Example

Figure 14:
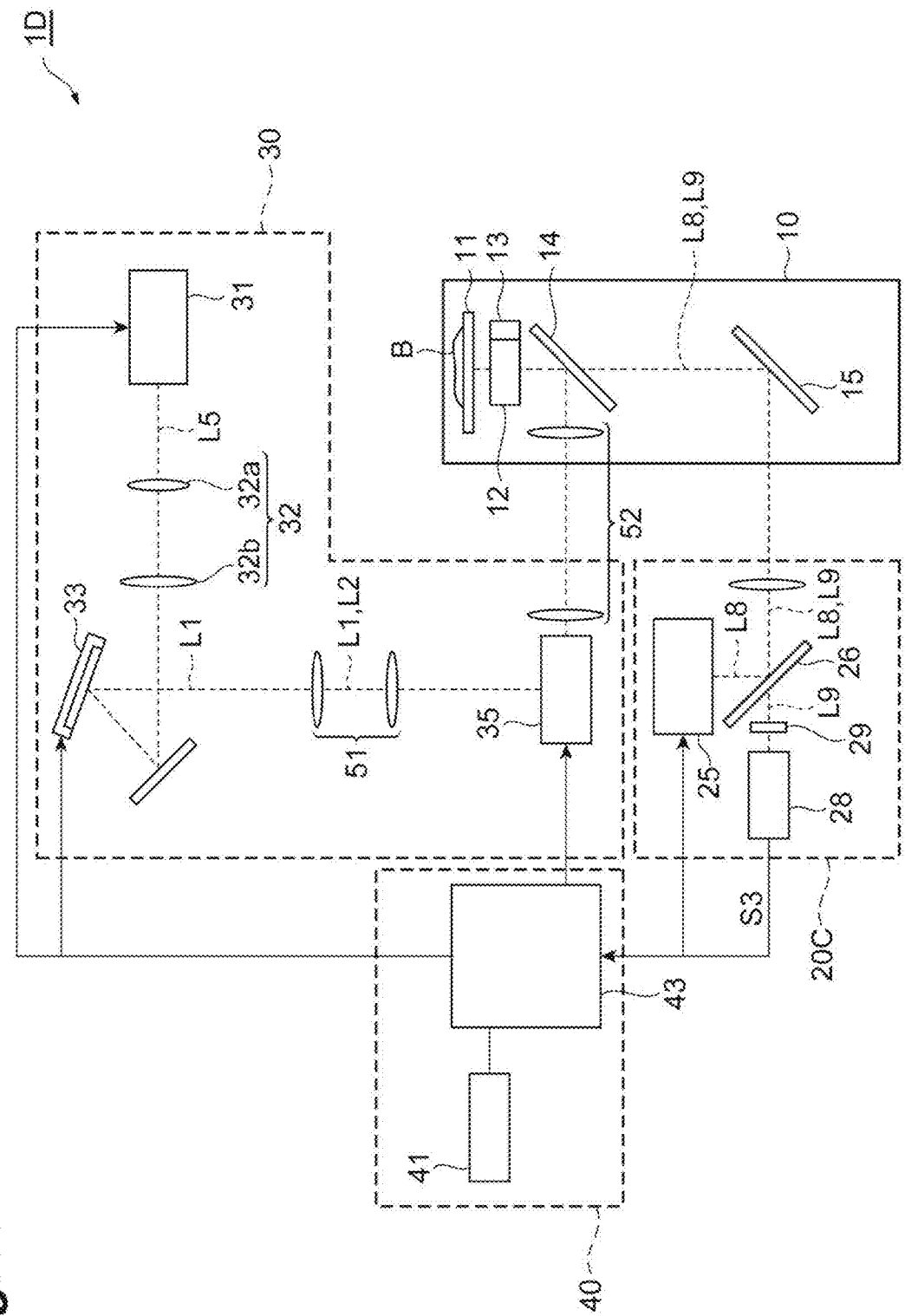
FIG. 14 is a diagram illustrating a configuration of a photostimulation apparatus according to a fourth modification example.

FIG. 14 is a diagram illustrating a configuration of a photostimulation apparatus 1D according to a fourth modification. In this modification example, an evanescent field is used for measurement of the surface shape of the biological object B. Accordingly, shape recognition such as recognition as to whether or not the biological object B is grounded to the biological object table 11 is facilitated. In this modification example, the objective tens 12 and the biological object table 11 (cover glass) in which total reflection occurs are used in order to generate an evanescent field.

In the photostimulation apparatus 1D of this modification example, the shape measurement unit 20C constitutes a shape acquisition unit. The shape measurement unit 20C includes a light source 25, a dichroic mirror 26, a detector 28, a filter 29, and a condensing lens 61. Configurations of the light source 25, the dichroic mirror 26, the detector 28, and the filter 29 are the same as those in the third modification example. The shape measurement unit 20C is optically coupled to the objective lens 12.

The condensing lens 61 is provided when the excitation light L8 is a surface illumination, and is disposed on the optical axis between the dichroic mirror 26 and the optical irradiation unit 10. The condensing lens 61 condenses the excitation light L8 on a rear focal plane of the objective lens 12. When the excitation light L8 is a point illumination, the condensing lens 61 is not necessary. In this case, for example, the excitation light L8 which is plane waves may be input to a region in which total reflection of the objective lens 12 occurs and the excitation light L8 may be scanned through parallel movement of the optical scanner or the biological object table 11. Further, a prism or an optical fiber may be used in place of the objective lens 12.

Fifth Modification Example

Figure 15:
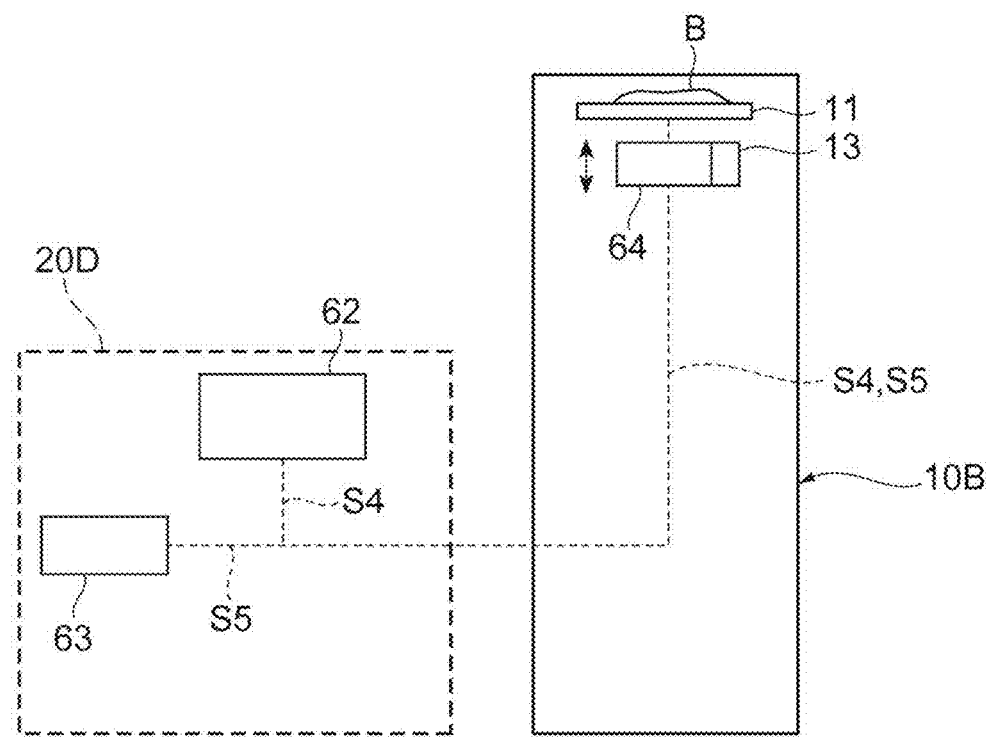
FIG. 15 is a diagram illustrating a configuration of an optical irradiation unit and a shape measurement unit of a photostimulation apparatus according to a fifth modification.

FIG. 15 is a diagram illustrating a configuration of an optical irradiation unit 10B and a shape measurement unit 20D of a photostimulation apparatus according to a fifth modification example. In this modification example, elasticity of the biological object B is measured using ultrasound, and a structure of the biological object B is obtained using an elasticity difference between regions of the biological object B. An aberration correction hologram is generated on the basis of the obtained structure. The irradiation light generation unit 30 and the control unit 40 illustrated in FIGS. 1 and 9 are not illustrated in FIG. 15.

As illustrated in FIG. 15, the shape measurement unit 20D of this modification example includes a pulse generation source 62 and a receiver 63 which is a detector. The pulse generation source 62 generates a pulse signal S4 for generating ultrasound. The receiver 63 receives the pulse signal S5 including information on an internal structure of the biological object B.

The optical irradiation unit 10B includes a lens with a piezoelectric thin film. 64 in place of the objective lens 12 of the optical irradiation unit 10 illustrated in FIG. 1. Other configurations are the same as those of the optical irradiation unit 10. The lens with the piezoelectric thin film 64 is disposed to face the biological object B, converts a pulse signal S4 to ultrasound using the piezoelectric thin film, irradiates the biological object B with the ultrasound, and converts the ultrasound reflected in the biological object B into a pulse signal S5. Although a common lens with a piezoelectric thin film is used for the pulse signal S4 and the pulse signal S5 in this modification example, a lens with a piezoelectric thin film for the pulse signal S4 and a lens with a piezoelectric thin film for the pulse signal S5 may be provided individually.

Sixth Modification Example

FIG. 16 is a diagram illustrating a configuration of a photostimulation apparatus 1E according to a sixth modification example. In this modification example, phase difference and differential interference are used for measurement of the surface shape of the biological object B. In the photostimulation apparatus 1E of this modification example, the shape measurement unit 20E constitutes a shape acquisition unit. The shape measurement unit 20E includes a light source 21, a beam splitter 22, a detector 24, a differential interference (DIC) prism 66, and a polarizer 67. The shape measurement unit 20E is optically coupled to the objective lens 12. A configuration of the light source 21, the beam splitter 22, and the detector 24 is the same as that in the first embodiment.

The DIC prism 66 and the polarizer 67 are arranged side by side on the optical path between the beam splitter 22 and the objective lens 12. The DIC prism 66 causes the light L3 from the light source 21 to separate in two, and also superposes return light L10 from the biological object B. The polarizer 67 limits the polarization of the lights L3 and L10. The light L10 reaching the beam splitter 22 from the biological object B via the DIC prism 66 and the polarizer 67 is transmitted through the beam splitter 22 and input to the detector 24.

The photostimulation apparatus and the photostimulation method according to an aspect of the present invention are not limited to the above-described embodiments, and various modifications may be made. For example, although the case in which the optical irradiation unit 10 is an inverted microscope has been described in the above embodiment, the optical irradiation unit 10 may be an upright microscope.

In place of the laser light source 31, an incoherent light source for outputting incoherent light may be used. The incoherent light source includes, for example, a super luminescent diode (SLD) or a light emitting diode (LED), an amplified spontaneous emission (ASE) light source, and a lamp-based light source.

INDUSTRIAL APPLICABILITY

According to aspects of the present invention, it is possible to provide a photostimulation apparatus and a photostimulation method capable of suppressing a decrease in condensing intensity of irradiation light inside a biological object and spreading of a condensing shape.

REFERENCE SIGNS LIST 1A to 1E: Photostimulation apparatus
10, 10B: Optical irradiation unit
11: Biological object table
12: Objective lens
13: Objective lens moving mechanism
14: Beam splitter
15: Reflective mirror
20, 20B to 20E, 60: Shape measurement unit
21: Coherent light source
22: Beam splitter
23: Reference light mirror
24: Detector
30: Irradiation light generation unit
31: Laser light source
32: Beam expander
33: Spatial light modulator
35: Optical scanner
40: Control unit
A2: Optical axis
B: Biological object
L1: irradiation light
L3: Coherent light
L4: Interference light

The invention claimed is:

1. A photostimulation apparatus for stimulating a biological object by irradiating with light, the photostimulation apparatus comprising:
    an objective lens arranged to face the biological object;
    a light source configured to output light with which the biological object is irradiated via the objective lens;
    a shape acquisition unit configured to acquire information on a shape of the biological object with a refractive index difference;
    a hologram generation unit configured to generate aberration correction hologram data for correcting an aberration due to the shape with the refractive index difference on the basis of the acquired information; and
    a spatial light modulator configured to modulate the light output from the light source based on the aberration correction hologram data.

2. The photostimulation apparatus according to claim 1, wherein the shape with the refractive index difference includes a surface shape of the biological object.

3. The photostimulation apparatus according to claim 1, wherein the shape with the refractive index difference includes a structure directly under a surface of the biological object.

4. The photostimulation apparatus according to claim 1, wherein the hologram generation unit is configured to perform a wavefront calculation using geometrical optics, wave optics, or electromagnetic field analysis to generate the aberration correction hologram data based on the information.

5. A photostimulation method for stimulating a biological object by irradiating with light, the method comprising:
    acquiring information on a shape of the biological object facing an objective lens with a refractive index difference;
    generating aberration correction hologram data for correcting aberrations due to the shape with the refractive index difference on the basis of the acquired information;
    controlling a spatial light modulator based on the aberration correction hologram data, modulating light output from a light source by the spatial light modulator; and
    stimulating the biological object by irradiating the biological object with the modulated light.

6. The photostimulation method according to claim 5, wherein the shape with the refractive index difference includes a surface shape of the biological object.

7. The photostimulation method according to claim 5, wherein the shape with the refractive index difference includes a structure directly under a surface of the biological object.

8. The photostimulation method according to claim 5, wherein, in the step of generating aberration correction hologram data, a wavefront calculation is performed using geometrical optics, wave optics, or electromagnetic field analysis to generating the aberration correction hologram data based on the information.

* * * * *